US010751089B2

(12) United States Patent  
Wigginton et al.

(10) Patent No.: US 10,751,089 B2  
(45) Date of Patent: Aug. 25, 2020

(54) ORTHOPEDIC STRUT WITH LOCKABLE SWIVEL HINGES

(71) Applicant: New Standard Device, LLC, San Antonio, TX (US)

(72) Inventors: Robert E. Wigginton, McKinney, TX (US); Bryant T. Phamvu, San Antonio, TX (US); C. Douglas Klein, Jr., Andover, MA (US)

(73) Assignee: New Standard Device, LLC, San Antonio, TX (US)

( * ) Notice: Subject to any disclaimer, the term of this patent is extended or adjusted under 35 U.S.C. 154(b) by 0 days.

(21) Appl. No.: 16/106,435

(22) Filed: Aug. 21, 2018

(65) Prior Publication Data

US 2018/0368888 A1    Dec. 27, 2018

(51) Int. Cl.
| | | |
|---|---|---|
| *A61B 17/64* | (2006.01) | |
| *A61B 17/66* | (2006.01) | |
| *A61B 17/62* | (2006.01) | |
| *A61B 17/00* | (2006.01) | |

(52) U.S. Cl.  
CPC .......... *A61B 17/6425* (2013.01); *A61B 17/62* (2013.01); *A61B 17/645* (2013.01); *A61B 17/6458* (2013.01); *A61B 17/6491* (2013.01); *A61B 17/66* (2013.01); *A61B 2017/00991* (2013.01)

(58) Field of Classification Search  
CPC ..... A61B 17/62; A61B 17/64; A61B 17/6425; A61B 17/6416; A61B 17/645; A61B 17/6475  
See application file for complete search history.

(56) References Cited

U.S. PATENT DOCUMENTS

| | | | | | |
|---|---|---|---|---|---|
| 4,308,863 | A | * | 1/1982 | Fischer | .................. A61B 17/62 606/56 |
| 6,030,386 | A | * | 2/2000 | Taylor | ..................... A61B 17/62 606/54 |
| 2010/0331840 | A1 | * | 12/2010 | Ross | .................. A61B 17/6475 606/54 |
| 2011/0208187 | A1 | * | 8/2011 | Wong | ................. A61B 17/6416 606/59 |

* cited by examiner

*Primary Examiner* — Julianna N Harvey  
(74) *Attorney, Agent, or Firm* — Gregory K. Goshorn; Greg Goshorn, P.C.

(57) ABSTRACT

Provided are a telescoping, adjustable orthopedic strut for use in conjunction with an external bone fixation (EBF) device and an EBF device that employs the strut. The strut includes swivel hinges at each end, wherein each swivel hinge is lockable in any position within a one hundred eighty degree (180°) plane and has a three hundred sixty degree (360°) angle of rotation with respect to an orthopedic plate of the EBF device; an outer sleeve; an inner sleeve configured to slide within the outer sleeve; wherein the inner sleeve and outer sleeve may be positioned and fixed with respect to each other to provide an acute adjustment of the length of the strut; a leadscrew threaded into the inner sleeve, wherein the lead screw can be either rotated or fixed in position to provide a fine adjustment of the length of the strut.

11 Claims, 7 Drawing Sheets

ORTHOPEDIC STRUT WITH LOCKABLE SWIVEL HINGES

FIELD OF THE DISCLOSURE

The claimed subject matter relates generally to an orthopedic strut with lockable swivel hinges and, more specifically, a telescoping adjustable strut with versatile hinge structures for use with an external bone fixation device.

BACKGROUND

External Bone Fixation (EBF) devices are employed in the treatment of bone deformity and acute trauma. Typical EBF devices use circular rings that surround a patient's limb. Adjustable connection rods and struts are employed to connect the circular rings together. Current connection rods have only a conical range of seven degrees (7°) and struts have only forty-seven degrees (47°), which reduces the functionality of the rods and struts, limiting the ability to connect circular rings together. Half pins and wires are employed to attach the circular rings to a patient's bone to stabilize the bone while the bone or bones are being corrected or healing. The half pins and wires attach to the EBF device at one or two points and are either drilled into or through a bone.

One well-known reconstructive EBF system is the Ilizarov frame, as shown in U.S. Pat. Nos. 4,365,624; 4,615,338; 4,978,348; 5,702,389 and 5,971,984. The Ilizarov frame uses a combination of circular frames, pins and wires for deformity correction.

SUMMARY

Provided are telescoping, adjustable struts for connecting plates employed in orthopedic external bone fixation (EBF) devices. The telescoping, adjustable struts incorporate lockable swivel hinges. The swivel hinges provide one hundred eighty degrees (180°) of movement in one direction and three hundred sixty degrees (360°) of rotation in another direction. A lockable swivel hinge is typically positioned on each end of a telescoping, adjustable strut. EBF devices, which employ the telescoping, adjustable struts, are used to fix broken bones and to stabilize bones that are being corrected or healing.

Provided are a telescoping, adjustable orthopedic strut for use in conjunction with an external bone fixation (EBF) device and an EBF device that employs the strut. The strut includes a plurality of swivel hinges, wherein each swivel hinge is lockable in any position within a one hundred eighty degree (180°) plane and a three hundred sixty degree (360°) angle of rotation with respect to an orthopedic plate of the EBF device; an outer sleeve; an inner sleeve configured to slide within the outer sleeve; wherein the inner sleeve and outer sleeve may be positioned with respect to each other and, when a fixation bolt is tightened, the inner sleeve and outer sleeve are secured with respect to each other to provide an acute adjustment; a leadscrew threaded into the inner sleeve; a jam nut threaded onto the leadscrew such that, when a jam nut is not tighten against a compression/distraction (C/D) nut, the leadscrew is free to rotate with respect to the C/D nut and inner sleeve and, when the jam nut is tightened against the C/D nut, the leadscrew is fixed, thereby providing a fine adjustment to an overall length of the strut; and a second swivel hinge of the plurality of swivel hinges coupled to an end of the leadscrew.

This summary is not intended as a comprehensive description of the claimed subject matter but, rather, is intended to provide a brief overview of some of the functionality associated therewith. Other systems, methods, functionality, features and advantages of the claimed subject matter will be or will become apparent to one with skill in the art upon examination of the following figures and detailed description.

BRIEF DESCRIPTION OF THE DRAWINGS

A better understanding of the claimed subject matter can be obtained when the following detailed description of the disclosed embodiments is considered in conjunction with the following figures.

DETAILED DESCRIPTION OF THE FIGURES

The illustrations and diagrams in the Figures illustrate the architecture, functionality, and operation of possible implementations of systems according to various embodiments of the present invention.

Figure 1:
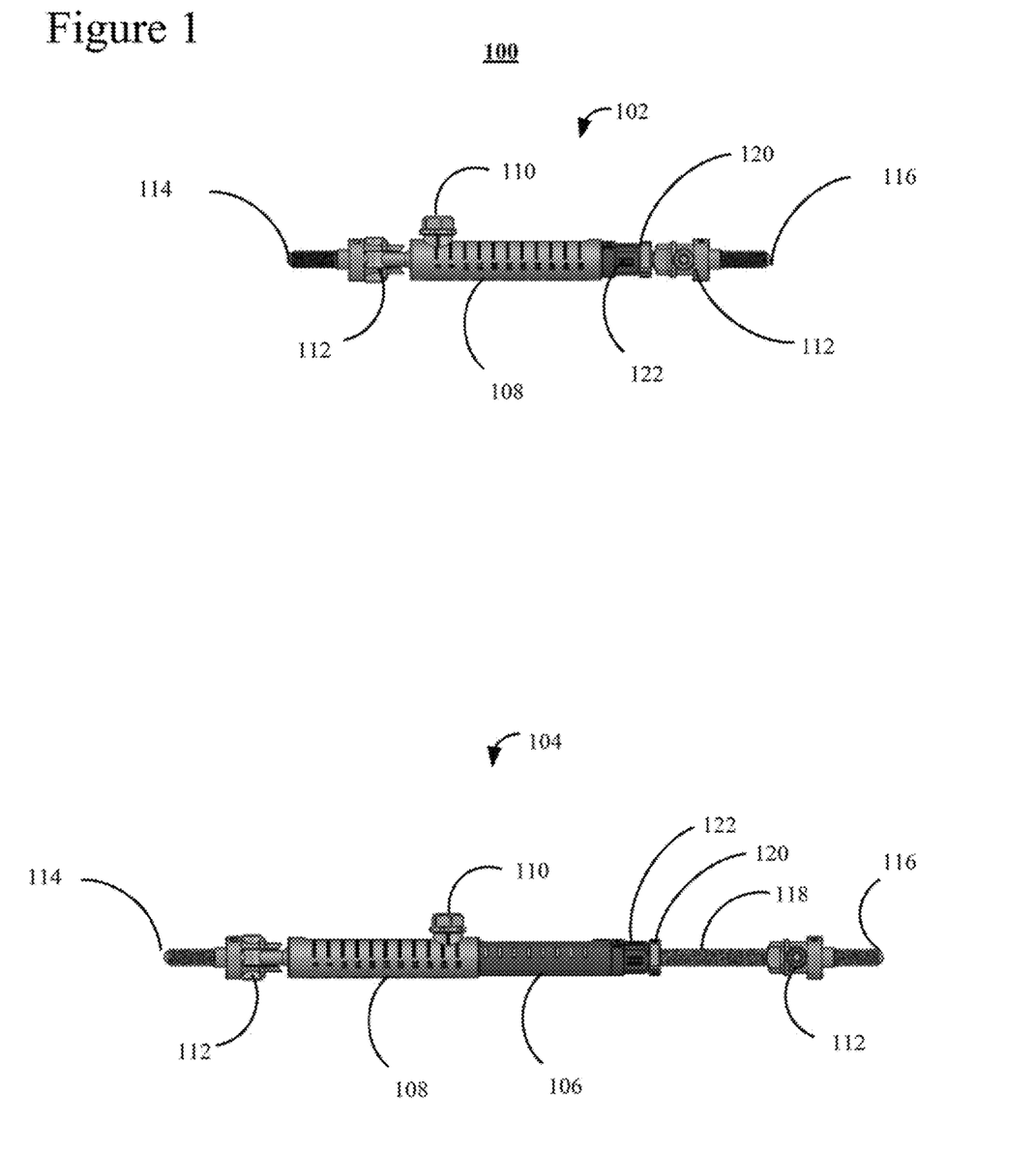
FIG. 1 is an illustration of two configurations of a telescoping, adjustable strut with lockable swivel hinges manufactured in accordance with the claimed subject matter.

Turning now to the figures, FIG. 1 is an illustration of two configurations of a telescoping, adjustable strut 100 with lockable swivel hinges manufactured in accordance with the claimed subject matter. A first configuration 102 shows strut 100 in a collapsed, or shortened position. A second configuration 104 shows strut 100 is an extended position. It should be understood that strut 100 may be configured, in addition to configurations 102 and 104, in any position in between shortened and extended positions 102 and 104.

An inner sleeve, or tube, 106, which is not visible in configuration 102, fits into an outer sleeve, or tube, 108. A fixation bolt 110, which is explained in more detail below in conjunction with FIG. 2, prevents inner sleeve 106 from moving with respect to outer sleeve 108 when bolt 110 is tightened. In this manner, the length of strut 100 may be easily be adjusted anywhere between the collapsed and extended positions 102 and 104. This adjustment of the length of strut 100 is called "acute" adjustment. At each end of strut 100 is a lockable swivel hinge 112 that is lockable in a one hundred eighty degrees (180°) and rotatable in three hundred sixty degrees (360°) when inserted into an orthopedic plate (see 136, FIGS. 3 and 4 and 212 and 216, FIG.

7). Lockable swivel hinge 112 is described in more detail below in conjunction with FIGS. 5 and 6.

For the sake of reference, the end of strut 100 on outer sleeve 108 side is labeled as a "stationary" end 114 and the end on inner sleeve 106 side as "moving" end 116. The terms "stationary" and "moving" are used because stationary end 114 doesn't rotate relative to outer sleeve or move in or out relative to outer sleeve 108 during adjustment of the length of strut 100. Moving end 116 is able to rotate three hundred sixty degrees (360°) by virtue of the fact that a leadscrew 118 may be rotated.

Visible in configuration 104, threaded rod, or "leadscrew," 118 threads into a jam nut 120 and a compression/distraction (C/D) nut 122. C/D nut 122 is pressed into and thereby attached to inner sleeve 106 such that C/D nut 122 is free rotate three hundred and sixty degrees (360°) with respect to inner sleeve 106. A care provider may accurately control the length of strut 100 by loosening jam nut 120, turning C/D 122 either clockwise or counterclockwise with respect to inner sleeve 106, thereby screwing leadscrew 118 either further into or out of inner sleeve 106, and tightening jam nut 120 against C/D nut 122 to both prevent leadscrew 118 from rotating and to lock the overall length of strut 100. This adjustment of the length of strut 100 is called "micro" or "fine" adjustment. Leadscrew 118, nut 120 and CD nut 122 provide a finer adjustment of the length of strut 100 than that provided by the acute adjustment of the relative positions of inner sleeve 106 and outer sleeve 108 as described above.

Figure 2:
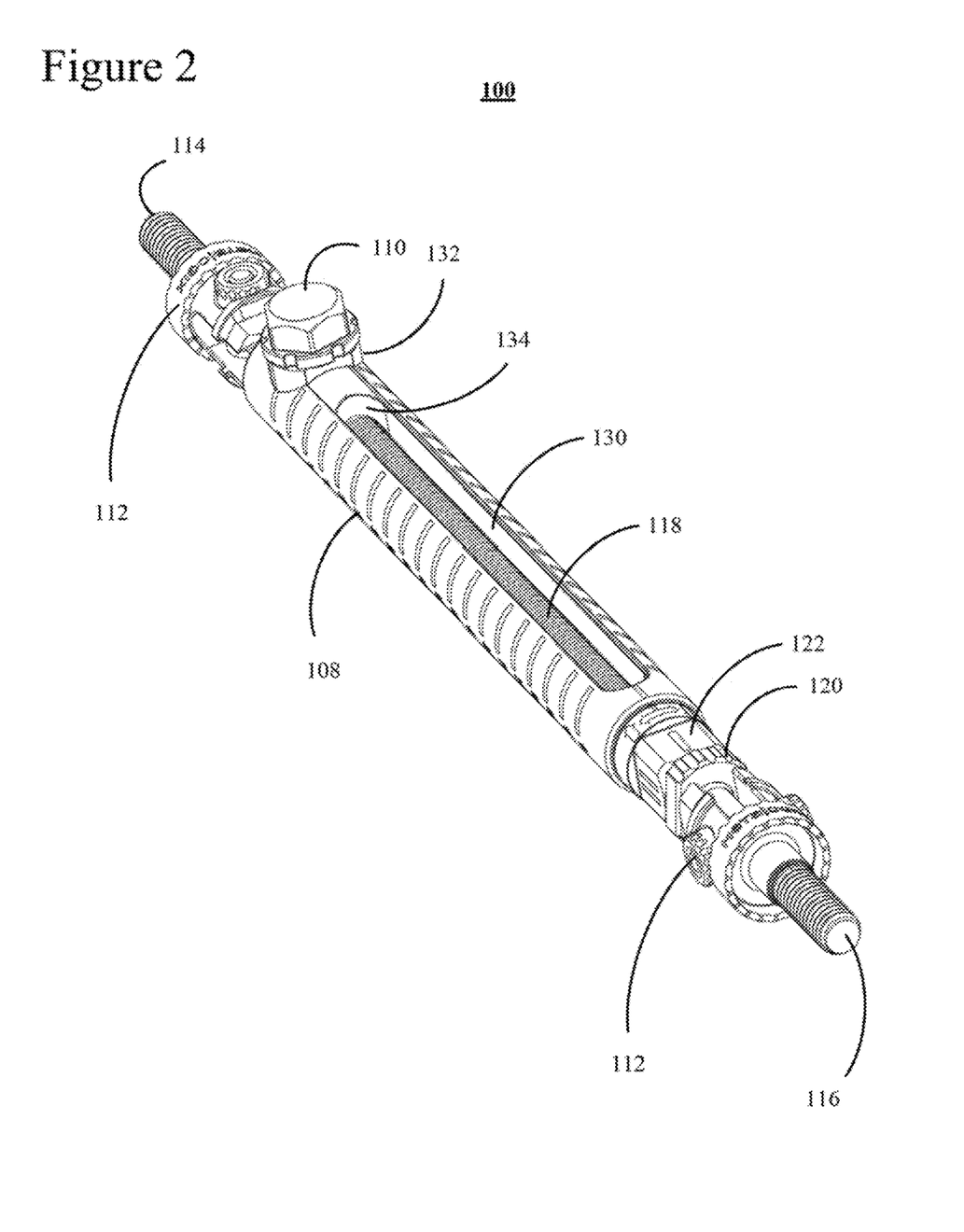
FIG. 2 is an illustration of the telescoping, adjustable strut, introduced in FIG. 1, from a perspective that shows additional details.

FIG. 2 is an illustration of strut 100, introduced in FIG. 1, from a perspective that shows additional details. Like FIG. 1, FIG. 2 shows outer sleeve 108, fixation bolt 110, swivel hinges 112, stationary end 114 and moving end 116. FIG. 2 shows strut 100 from an angle that shows an opening, or groove, 130 in outer sleeve 108 (FIG. 1) through which fixation bolt 110 is positioned. Fixation bolt 110 passes through opening 130, a clamping washer 132 and is treaded into inner sleeve 106 (FIG. 1), only a portion 134 of which is visible in FIG. 2. Washer 132 is configured to be flat on one side and conform to the curvature of outer sleeve 108 on a second side. When fixation bolt 110 is loosened, inner sleeve 106 and outer sleeve 108 may be easily moved with respect to each other. When fixation bolt 110 is tightened, outer sleeve 108 is compressed between washer 132 and inner sleeve 106, thereby preventing inner sleeve 106 and outer sleeve 108 from moving with respect to each other thereby providing an acute adjustment of strut 100.

Also illustrated in FIG. 2 is leadscrew 118 (FIG. 1) which is threaded into C/D nut 122, which is pressed fitted into inner tube 106, and jam nut 120. Leadscrew 118 is coupled to swivel hinge 112 that terminates at moving end 116 (FIG. 1). As explained above in conjunction with FIG. 1, a care provider may make a micro adjustment of strut 100 by loosening jam nut 120, turning C/D nut 122 and then tightening jam nut 120 against C/D nut 122.

Figure 3:
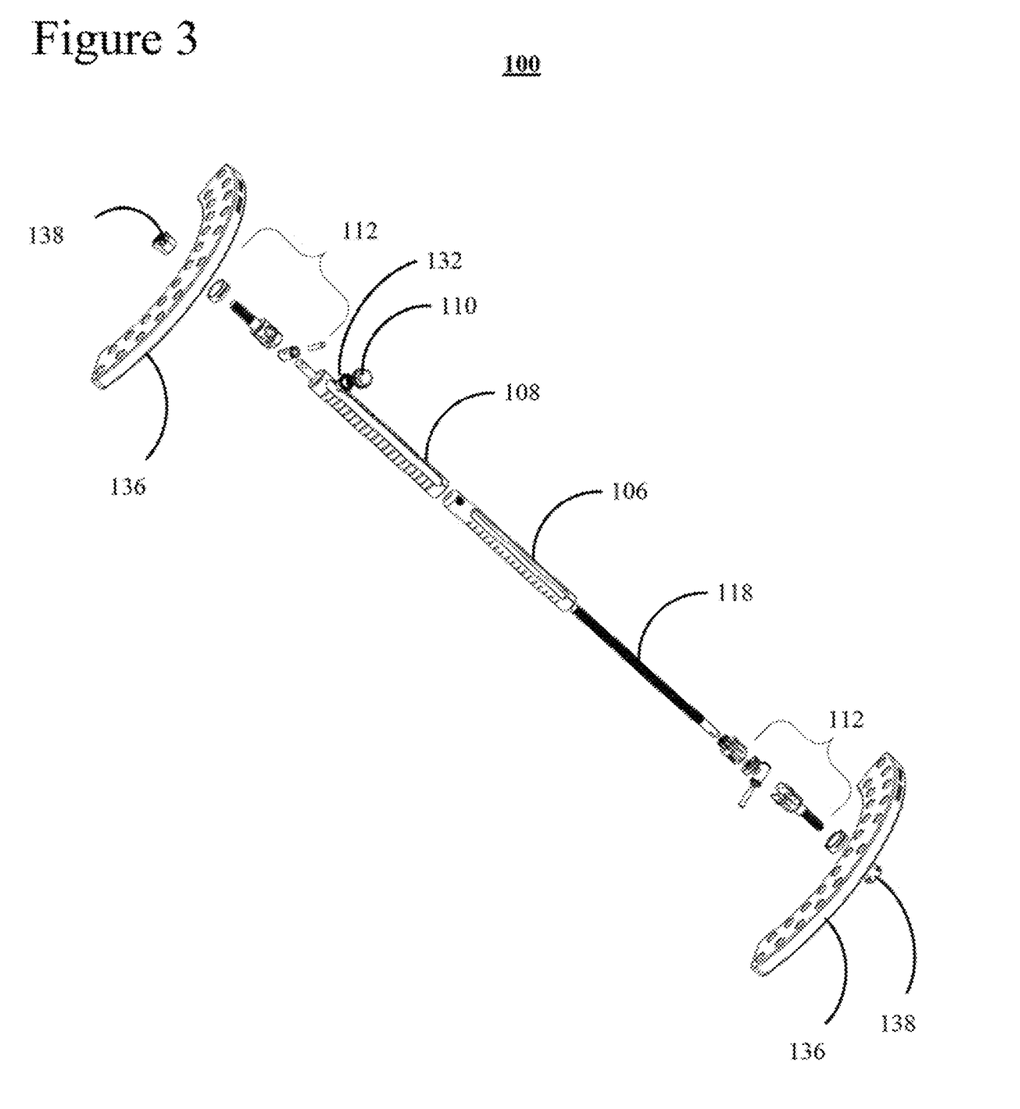
FIG. 3 is an illustration of the telescoping, adjustable strut, shown in FIGS. 1 and 2, disassembled to show individual components more clearly.

FIG. 3 is an illustration of strut 100, shown in FIGS. 1 and 2, disassembled to show individual components more clearly. Also illustrated are two (2) orthopedic plates 136 that might be connected with strut 100 as part of a part of an External Bone Fixation (EBF) device (see 200, FIG. 7). Like FIG. 2, FIG. 3 shows inner sleeve 106, outer sleeve 108, fixation bolt 110, clamping washer 132, leadscrew 118 and swivel hinges 112, which in this view are also disassembled (see FIG. 5). Also shown are two (2) speed nuts 138 that are employed to attach swivel hinges 112 to orthopedic plates 136.

Figure 4:
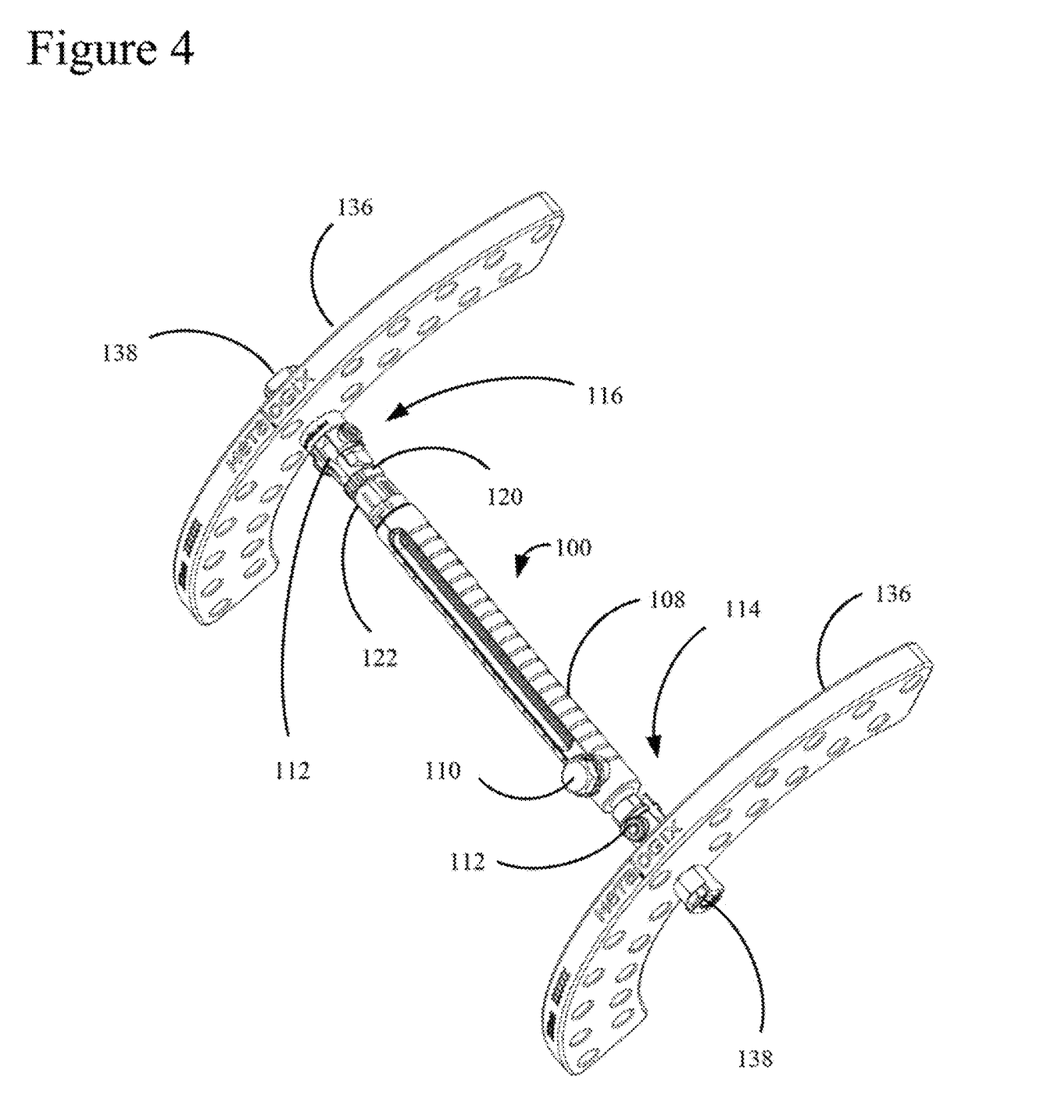
FIG. 4 is an illustration of the telescoping, adjustable strut, described in conjunction with FIGS. 1-3, connecting two orthopedic plates.

FIG. 4 is an illustration of strut 100, described in conjunction with FIG. 1-3, connecting orthopedic plates 136 (FIG. 3). In this figure, strut 100 is configured in shortened configuration, or position, 102 (FIG. 1). Strut 100 is secured to orthopedic plates 136 (FIG. 3) with speed nuts 138 (FIG. 3) screwed onto compression threads 144 (FIGS. 5 and 6), which are obscured in FIG. 4. Like FIGS. 1-3, FIG. 4 shows fixation bolt 110, outer sleeve 108 (inner sleeve 106 is obscured in shortened position 102), swivel hinges 112, stationary end 114, moving end 116, jam nut 120 and C/D nut 122.

Figure 5:
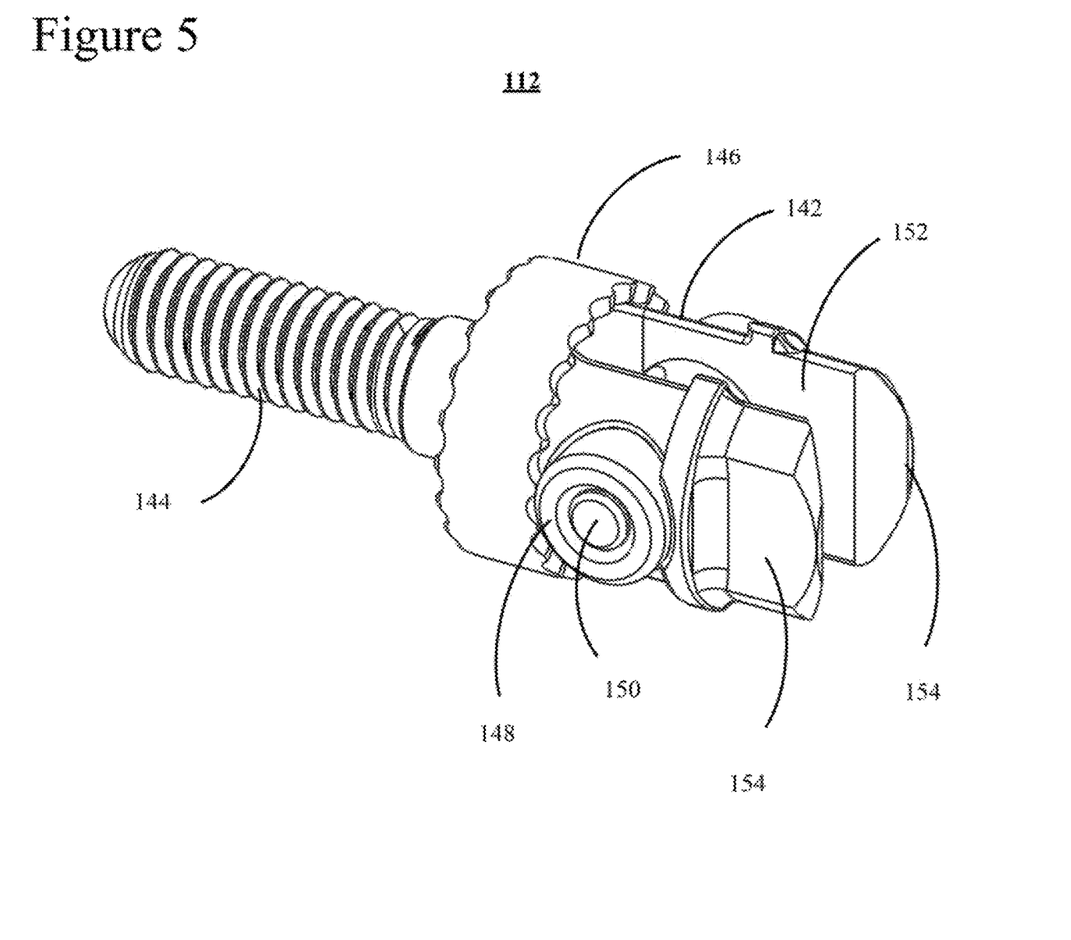
FIG. 5 is an illustration of a lockable swivel hinge, first introduced in FIG. 1, in greater detail.

FIG. 5 is an illustration of lockable swivel hinge 112, first introduced in FIG. 1, in greater detail. Hinge 112 includes a body 142 with a threaded portion, or compression threads, 144. Compression threads 144 is used to attach hinge 112 to an orthopedic plate (see 136, FIGS. 3 and 4 and 212, 216, FIG. 7). Compression threads 144 pass through a hole (not shown) in an orthopedic plate, which is then secured with a speed nut (138, FIGS. 3 and 4). In addition to securing strut 100 to the orthopedic plate, speed nut 138 presses a locking collar 146 against a swivel pin 148, thereby locking swivel pin 148 and body 142 within a one hundred eighty degree (180°) arc with respect to compression either leadscrew 118 (FIGS. 1-3) or outer sleeve 108 (FIGS. 1-4). In addition, body 142 may be rotated with respect to orthopedic plates 136 and locked in any position, i.e., body 142 is rotatable orthogonally three hundred sixty degrees (360°) with respect to orthopedic plates 136 by virtue of the fact that, on stationary end 114 (FIGS. 1-3), outer sleeve 108 may be rotated and, on moving end 116 (FIGS. 1-3), leadscrew 118 may be rotated.

A locking, or dowel, pin 150 is inserted through swivel pin 148 so that either leadscrew 118 (FIG. 1-3) or outer sleeve 108 (FIGS. 1-3) is securely attached to a respective lockable swivel hinge 112. A channel 152 in body 142 provides space for either leadscrew 118 or outer sleeve 108 to be inserted into moving end 116 (FIGS. 1-3) or fixed end 114 (FIGS. 1-3), respectively, to be mounted and enables swivel hinge 112 be positioned within a one hundred eighty degree (180°) arc. A parallel pair of surfaces 154, one of which is obscured by the orientation of lockable swivel pin 112, provide a means to place a wrench (not shown) while tightening locking collar 146 against swivel pin 148 with speed nut 138.

Figure 6:
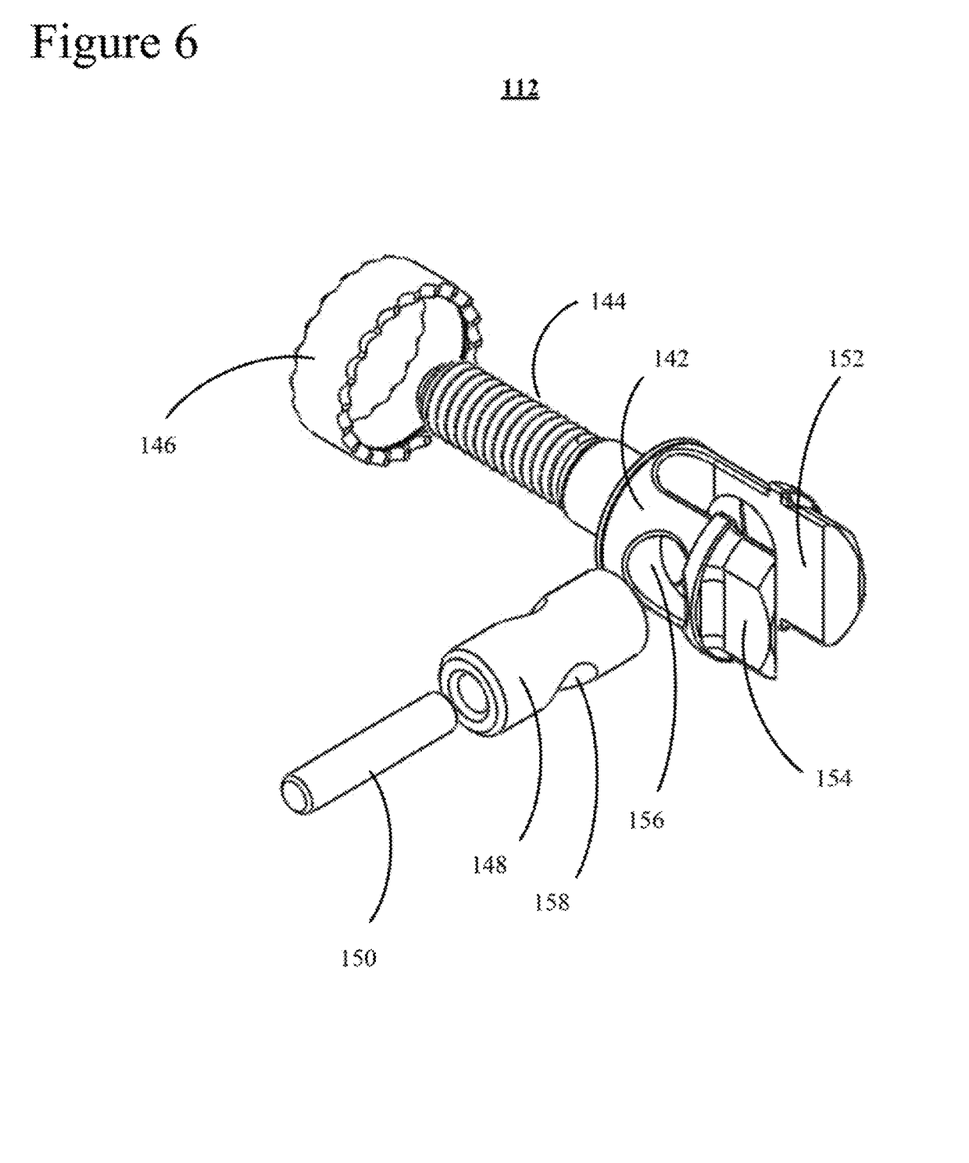
FIG. 6 is an illustration of the lockable swivel hinge of FIGS. 1-5 disassembled to more clearly show the component parts.

FIG. 6 is an illustration of the lockable swivel hinge 112 of FIGS. 1-5 disassembled to more clearly show component parts. Included are body 142, compression threads 144, locking collar 146, swivel pin 148, lock pin 150, channel 152 and parallel surfaces 154, all of which were introduced in FIG. 5. At stationary end 114 (FIGS. 1-4) of strut 100 (FIGS. 1-4), a portion (not shown) of outer sleeve 108 (FIGS. 1 & 2) extends into channel 152. Swivel pin 148 extends through a hole 156 of body 142 and the extended portion of outer sleeve 108 passes through a hole 158 in swivel pin 148. The extended portion of outer sleeve 108 is then locked into place by press fitting pin 150 through the center of swivel pin 148 and through a hole (not shown) in the extended portion of outer sleeve 108.

In a similar fashion, swivel hinge 112 is attached to leadscrew 118 (FIGS. 1-4) at moving end 116 (FIGS. 1-4). Leadscrew 118 extends into channel 152. Swivel pin 148 is inserted into hole 156 of body 142 and leadscrew 118 passes through hole 158 in swivel pin 148. Leadscrew 118 is then locked into place by press fitting pin 150 through the center of swivel pin 148 and through a hole (not shown) in leadscrew 118.

Figure 7:
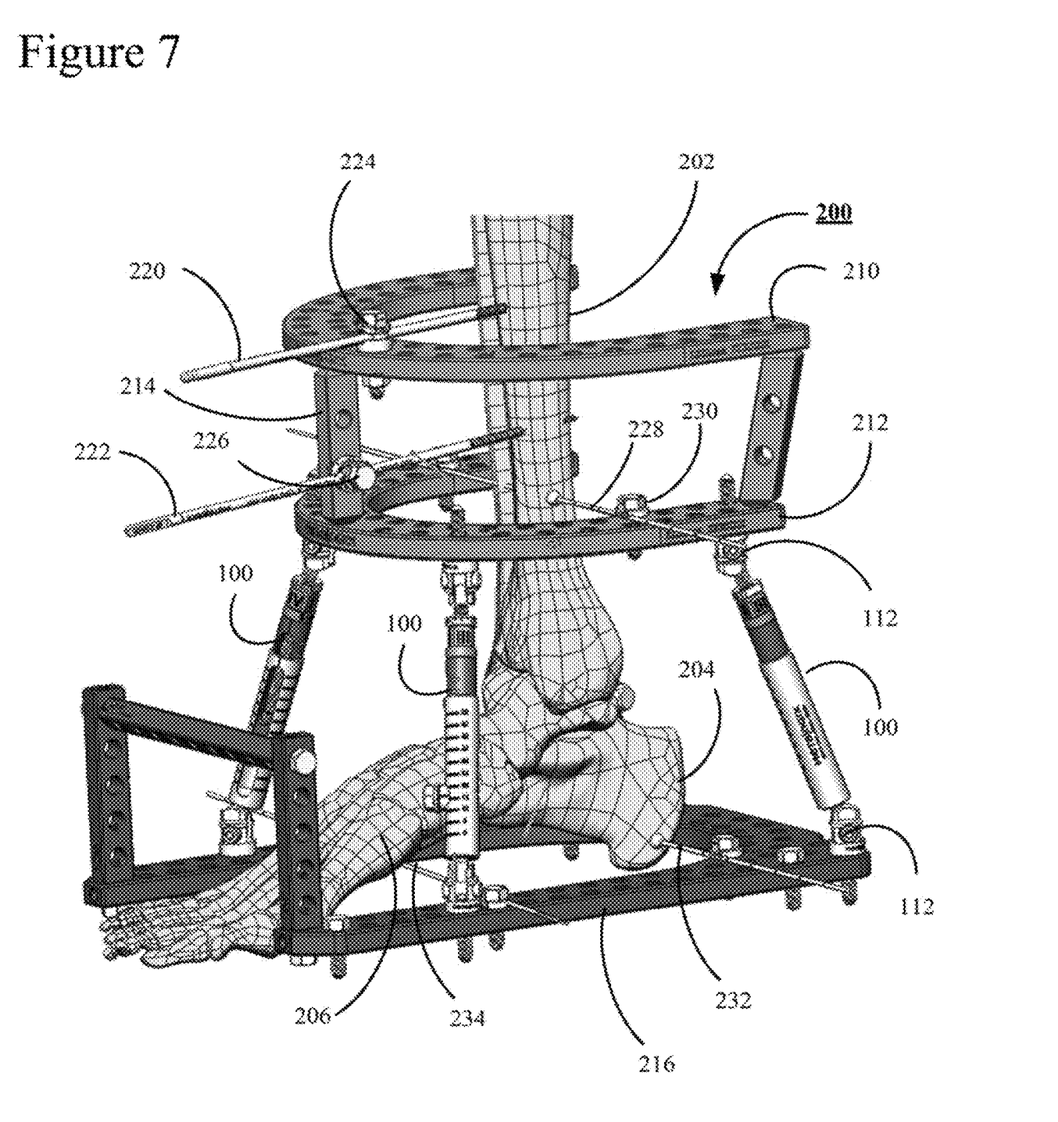
FIG. 7 is an illustration of an illustration of an External Bone Fixation (EBF) device, attached to a patient's foot and leg bones, that employs the telescoping, adjustable strut shown in FIGS. 1-4 and the lockable swivel hinge shown in FIGS. 1-6.

FIG. 7 is an illustration of an illustration of an External Bone Fixation (EBF) device 200, attached to a patient's leg bone 202, heal bone 204 and foot bone 206, that employs telescoping, adjustable strut 100 shown in FIGS. 1 and 2 and the lockable swivel hinge 112 shown in FIGS. 1-4. EBF device 200 includes a number of frame elements, such as a frame elements 210, 212, 214 and 216.

FIG. 7 shows three of four telescoping, adjustable struts 100 with the fourth being obscured by bones 202, 204 and 206. In this example, struts 100 attach to frame elements 212 and 216 although that may also be employed to attach to other frame elements, both those illustrated and ones not illustrated but familiar to persons skilled in the relevant arts as well.

EBF device 200 is attached to leg bone 202 with two (2) pins, a pin 220 and a pin 222. Pins 220 and 222 are attached to EBF device 200 with fixation bolts 224 and 226 on frame elements 210 and 214, respectively. EBF device 200 is also attached to leg bone 202 with an orthopedic wire 228, attached by means of a fixation bolt 230 on frame element 212. Although not clearly visible in FIG. 4, in this example, wire 228 passes through leg bone 202 and is also attached to EBF device 200 at a second point with a fixation bolt (not shown) on the opposite of side of leg bone 202 than fixation bolt 230. In a similar fashion, orthopedic wires 232 and 234 attach frame element 216 of EBF device 200 to ankle bone 204 and foot bone 206, respectively. By adjusting the length of struts 100, as described above in conjunction with FIGS. 1-4, and the orientation of swivel hinges 112, the positions of orthopedic plates such as plates 212 and 216 can be customized for a specific patient and treatment.

While the claimed subject matter has been shown and described with reference to particular embodiments thereof, it will be understood by those skilled in the art that the foregoing and other changes in form and detail may be made therein without departing from the spirit and scope of the claimed subject matter, including but not limited to additional, less or modified elements.

We claim:

1. A telescoping, adjustable orthopedic strut for use in conjunction with an external bone fixation (EBF) device, comprising:
   a plurality of swivel hinges, each swivel hinge comprising:
      a body;
      a channel within the body;
      a threaded portion coupled to the body;
      a locking collar, wherein the locking collar is placed over the threaded portion; and
      a speed nut;
      wherein each swivel hinge is lockable in any position within a one hundred eighty degree (180°) plane within the channel and a three hundred sixty degree (360°) angle of rotation with respect to an orthopedic plate of the EBF device;
   an outer sleeve; comprising:
      a groove extending through the outer sleeve; and
      a compression/distraction (C/D) nut attached to a first end of the outer sleeve and configured to rotate three hundred and sixty degrees (360°) with respect to the outer sleeve;
      wherein a first swivel hinge of the plurality of swivel hinges is coupled to a second end of the outer sleeve, the second end opposite the first end;
   an inner sleeve configured to slide within the outer sleeve;
   a fixation bolt that passes through the groove and threads into the inner sleeve such that, when the fixation bolt is loosened, the inner sleeve and outer sleeve may be positioned with respect to each other and, when the fixation bolt is tightened, the inner sleeve and outer sleeve are secured with respect to each other thereby providing an acute adjustment to an overall length of the strut;
   a leadscrew threaded through the C/D nut such that a first portion of the leadscrew extends into the inner sleeve and a second portion of the leadscrew is positioned outside the inner sleeve;
   a jam nut threaded onto the leadscrew such that the leadscrew is fixed into position with respect to the C/D nut when the jam nut is tighten against the C/D nut and the leadscrew is free to rotate with respect to the C/D nut when the jam nut is not tightened against the C/D nut, thereby providing a fine adjustment to an overall length of the strut; and
   a second swivel hinge of the plurality of swivel hinges coupled to an end of the lead screw corresponding to the second portion.

2. The telescoping, adjustable orthopedic strut of claim 1, each swivel hinge further comprising a swivel pin, wherein the swivel pin attaches the body to a corresponding outer sleeve or leadscrew.

3. The telescoping, adjustable orthopedic strut of claim 2, each swivel hinge further comprising a lock pin, wherein the lock pin secures the swivel pin to the body and the corresponding outer sleeve or leadscrew.

4. The telescoping, adjustable orthopedic strut of claim 2, wherein the speed nut, when tightened against an orthopedic frame element, presses the locking collar against the swivel pin to fix the swivel pin into both a particular angle of the one hundred eighty degree (180°) plane and a particular angle of the three hundred and sixty degrees (360°) of rotation.

5. The telescoping, adjustable orthopedic strut of claim 1, further comprising a clamping washer, wherein the fixation bolt passes through the clamping washer and the outer sleeve and, wherein when the fixation bolt is tightened, the clamping washer is compressed between the fixation bolt and the outer sleeve.

6. An external bone fixation (EBF) device, comprising
   a plurality of at least two orthopedic plates; and
   a plurality of at least two telescoping, adjustable orthopedic struts coupling two of the plurality of orthopedic plates, each strut comprising:
      a plurality of swivel hinges, each swivel hinge comprising:
         a body;
         a channel within the body;
         a threaded portion coupled to the body;
         a locking collar, wherein the locking collar is placed over the threaded portion; and
         a speed nut;
         wherein each swivel hinge is lockable in any position within a one hundred eighty degree (180°) plane within the channel and a three hundred sixty degree (360°) angle of rotation with respect to a corresponding orthopedic plate of the two orthopedic plates;
      an outer sleeve; comprising:
         a groove extending through the outer sleeve; and
         a compression/distraction (C/D) nut attached to a first end of the outer sleeve and configured to rotate three hundred and sixty degrees (360°) with respect to the outer sleeve;

wherein a first swivel hinge of the plurality of swivel hinges is coupled to a second end of the outer sleeve, the second end opposite the first end;

an inner sleeve configured to slide within the outer sleeve;

a fixation bolt that passes through the groove and threads into the inner sleeve such that, when the fixation bolt is loosened, the inner sleeve and outer sleeve may be positioned with respect to each other and, when the fixation bolt is tightened, the inner sleeve and outer sleeve are secured with respect to each other thereby providing an acute adjustment to an overall length of the strut;

a leadscrew threaded through the C/D nut such that a first portion of the leadscrew extends into the inner sleeve and a second portion of the leadscrew is positioned outside the inner sleeve;

a jam nut threaded onto the leadscrew such that the leadscrew is fixed into position with respect to the C/D nut when the jam nut is tighten against the C/D nut and the leadscrew is free to rotate with respect to the C/D nut when the jam nut is not tightened against the C/D nut, thereby providing a fine adjustment to an overall length of the strut; and a second swivel hinge of the plurality of swivel hinges coupled to an end of the lead screw corresponding to the second portion.

7. The external bone fixation (EBF) device of claim 6, each swivel hinge further comprising a swivel pin, wherein the swivel pin attaches the body to a corresponding outer sleeve or leadscrew.

8. The external bone fixation (EBF) device of claim 7, each swivel hinge further comprising a lock pin, wherein the lock pin secures the swivel pin to the body and the corresponding outer sleeve or leadscrew.

9. The external bone fixation (EBF) device of claim 7, wherein the speed nut, when tightened against a corresponding orthopedic plate, presses the locking collar against the swivel pin to fix the swivel pin into both a particular angle of the one hundred eighty degree (180°) plane and a particular angle of the three hundred and sixty degrees (360°) of rotation.

10. The external bone fixation (EBF) device of claim 6, further comprising a clamping washer, wherein the fixation bolt passes through the clamping washer and the outer sleeve and, wherein when the fixation bolt is tightened, the clamping washer is compressed between the fixation bolt and the outer sleeve.

11. A telescoping, adjustable orthopedic strut for use in conjunction with an external bone fixation (EBF) device, comprising:

a plurality of swivel hinges, each swivel hinge comprising:

a body;

a channel within the body;

a threaded portion coupled to the body;

a locking collar, wherein the locking collar is placed over the threaded portion;

a swivel pin;

a lock pin; and a speed nut;

wherein each swivel hinge is lockable in any position within a one hundred eighty degree (180°) plane within the channel and a three hundred sixty degree (360°) angle of rotation with respect to an orthopedic plate of the EBF device; and wherein the speed nut, when tightened against a corresponding orthopedic plate of the EBF device, presses the locking collar against the swivel pin to fix the swivel pin into both a particular angle of the one hundred eighty degree (180°) plane and a particular angle of the three hundred and sixty degrees (360°) of rotation;

an outer sleeve; comprising:

a groove extending through the outer sleeve; and a compression/distraction (C/D) nut attached to a first end of the outer sleeve and configured to rotate three hundred and sixty degrees (360°) with respect to the outer sleeve;

wherein a first swivel hinge of the plurality of swivel hinges is coupled to a second end of the outer sleeve, the second end opposite the first end;

an inner sleeve configured to slide within the outer sleeve;

a fixation bolt that passes through the groove and threads into the inner sleeve such that, when the fixation bolt is loosened, the inner sleeve and outer sleeve may be positioned with respect to each other and, when the fixation bolt is tightened, the inner sleeve and outer sleeve are secured with respect to each other thereby providing an acute adjustment to an overall length of the strut;

a leadscrew threaded through the C/D nut such that a first portion of the leadscrew extends into the inner sleeve and a second portion of the leadscrew is positioned outside the inner sleeve;

a jam nut threaded onto the leadscrew such that the leadscrew is fixed into position with respect to the C/D nut when the jam nut is tighten against the C/D nut and the leadscrew is free to rotate with respect to the C/D nut when the jam nut is not tightened against the C/D nut, thereby providing a fine adjustment to an overall length of the strut; and a second swivel hinge of the plurality of swivel hinges coupled to an end of the lead screw corresponding to the second portion.

* * * * *